(12) United States Patent
Trksak et al.

(10) Patent No.: US 7,829,600 B1
(45) Date of Patent: Nov. 9, 2010

(54) ALKENYL SUCCINIC ACID ANHYDRIDE HALF ESTER EMULSIFIER

(75) Inventors: Ralph Trksak, Manville, NJ (US); Afaf Makarious, Dayton, NJ (US)

(73) Assignee: Brunob II B.V., Arnheim (NL)

( * ) Notice: Subject to any disclaimer, the term of this patent is extended or adjusted under 35 U.S.C. 154(b) by 0 days.

(21) Appl. No.: 12/687,782

(22) Filed: Jan. 14, 2010

Related U.S. Application Data (63) Continuation of application No. 12/626,463, filed on Nov. 25, 2009.

(51) Int. Cl.
| | |
|---|---|
| B01F 17/36 | (2006.01) |
| B01F 17/00 | (2006.01) |
| C08B 31/04 | (2006.01) |
| C08B 33/02 | (2006.01) |
| C08B 35/02 | (2006.01) |
| A23L 2/00 | (2006.01) |
| A23L 2/06 | (2006.01) |
| B01F 3/08 | (2006.01) |
| A61Q 13/00 | (2006.01) |
| A61K 47/14 | (2006.01) |
| A61K 47/26 | (2006.01) |
| C11D 3/22 | (2006.01) |

(52) U.S. Cl. .................. 516/73; 516/105; 536/102; 536/103; 536/107; 536/110; 426/590; 426/599; 426/616; 426/650; 426/651; 426/658; 426/661; 512/2; 514/778; 514/938; 514/939; 510/470; 510/474

(58) Field of Classification Search ............ 516/28, 516/29, 73, 105; 536/102, 103, 107, 110, 536/112; 426/590, 599, 616, 650, 651, 658, 426/661; 512/2; 514/778, 938, 939; 510/470, 510/474

See application file for complete search history.

(56) References Cited

U.S. PATENT DOCUMENTS

| | | | |
|---|---|---|---|
| 2,661,349 A | | 12/1953 | Caldwell et al. |
| 3,455,838 A | * | 7/1969 | Marotta et al. ........... 428/402.2 |
| 3,732,207 A | | 5/1973 | Kovats |
| 4,460,617 A | * | 7/1984 | Barndt et al. ............. 426/661 |

(Continued)

FOREIGN PATENT DOCUMENTS

WO      0116348      3/2001

(Continued)

OTHER PUBLICATIONS

Chee Teck Tan, "Beverage Flavor Emulsion—A Form of Emulsion Liquid Membrane Microencapsulation", Food Flavors: Analysis and Pakaging Influences, E. T. Contis et al Editors, (copyright 1998—month unknown), Elsevier Science, pp. 29-42.*

(Continued)

*Primary Examiner*—Daniel S Metzmaier
(74) *Attorney, Agent, or Firm*—Karen G. Kaiser (57) ABSTRACT

The present invention relates to a starch emulsifier product prepared by sufficiently solubilizing a starch and subsequently sufficiently derivatizing the sufficiently solubilized starch product, in one embodiment by reacting the sufficiently solubilized starch with an alkenyl succinic anhydride. Such starch emulsifier products are useful as emulsifying and/or encapsulating agents, particularly in systems where high load and retention of the active ingredient, low surface oil exposure, and excellent oxidation resistance is desired.

20 Claims, 1 Drawing Sheet

U.S. PATENT DOCUMENTS

| | | | | |
|---|---|---|---|---|
| 4,845,152 | A * | 7/1989 | Palmer | 524/734 |
| 4,977,252 | A | 12/1990 | Chiu | |
| 5,185,176 | A | 2/1993 | Chiu | |
| 5,354,559 | A * | 10/1994 | Morehouse | 536/110 |
| 5,616,358 | A * | 4/1997 | Taylor et al. | 426/590 |
| 6,372,361 | B1 * | 4/2002 | Mackewicz et al. | 428/537.5 |
| 6,809,197 | B1 * | 10/2004 | Woo et al. | 536/106 |
| 7,157,573 | B2 | 1/2007 | Buwalda et al. | |
| 2002/0142087 | A1 | 10/2002 | Trubiano et al. | |
| 2004/0247658 | A1 * | 12/2004 | Trubiano et al. | 424/450 |
| 2005/0208009 | A1 * | 9/2005 | Bonnardel et al. | 424/70.13 |

FOREIGN PATENT DOCUMENTS

WO     2007008066     7/2007

OTHER PUBLICATIONS

S. Tesch et al., "Stabilization of emulsions by OSA starches", Journal of Food Engineering 54 (2002—month unknown) pp. 167-174 (online @ http://www.sciencedirect.com/ , downloaded Apr. 29, 2010).*

Chee Teck Tan, "Chapter 12 Beverage Emulsion", Food Emulsions, 4$^{th}$ Edition, Revised and Expanded, Edited by Stig Friberg, Kåre Larsson, Kare Larsson, Johan Sjöblom, Marcel Dekker, Inc., NY, NY (Copyright 2004—month unavailable), pp. 1-40, (obtained online @ http://books.google.com/books—downloaded Apr. 29, 2010).*

* cited by examiner

Figure

ALKENYL SUCCINIC ACID ANHYDRIDE HALF ESTER EMULSIFIER

CROSS-REFERENCE TO RELATED APPLICATIONS

This application is a continuation of and claims priority to U.S. Nonprovisional patent application Ser. No. 12/626,463, filed with the United States Patent and Trademark office on Nov. 25, 2009, now pending.

BACKGROUND OF THE INVENTION

This invention relates to the preparation of a novel emulsifier; emulsions prepared with the emulsifier; and products prepared utilizing the emulsifier. Half-ester starch derivatives may be created by reacting starch and a substituted dicarboxylic acid anhydride so as to form alkenyl succinic anhydride starch derivatives. Native starch granules are insoluble in cold water. When native starch granules are dispersed in water and heated, however, they become hydrated and swell. With continued heating, shear, or conditions of extreme pH, the granules fragment and the starch molecules are dispersed in the water, i.e., solubilized, resulting in a nongranular, dispersed starch.

BRIEF SUMMARY OF THE INVENTION

In one embodiment, the invention comprises an emulsifier product that is a starch half ester of an alkenyl succinic anhydride. The starch half ester of an alkenyl succinic anhydride has a water fluidity of no more than 75, is prepared by a dispersed phase process, and, when used to prepare a test oil-in-water emulsion with the starch half ester of an alkenyl succinic anhydride as a sole emulsifier at a w/w ratio of the starch half ester of an alkeny succinic anhydride:oil of 1:4 with a 20% oil load, creates a test oil-in-water emulsion characterized by at least the following: a) no more than about 5% of the oil particles of the emulsion greater than 1 μm after 24 hours at 57 C as assessed by polarization intensity differential plus elastic light scattering; and b) a Brookfield viscosity of the emulsion of less than about 2000 cps after about one week of storage at 5 C, as assessed by Brookfield Programmable DV-1 Viscometer.

In another embodiment, the starch emulsifier product is a half ester of dodecenyl or octenyl succinic anhydride.

In another embodiment, the water fluidity of the starch emulsifier product is not greater than 65.

In another embodiment, the water fluidity of the starch emulsifier product is not greater than 40.

In another embodiment, the water fluidity of the starch emulsifier product is not greater than 20.

In another embodiment, the starch emulsifier product is a half ester of an octenyl succinic anhydride and the water fluidity of the starch emulsifier product is not greater than 40.

In another embodiment, the average particle size of the starch emulsifier product may be characterized as less than one micron, as assessed by Polarization Intensity Differential Plus Elastic Light Scattering (Beckman Coulter LS 13 320 Aqueous Module).

In another embodiment, a test oil-in-water emulsion prepared using the starch emulsifier product as a sole emulsifier is characterized by having a ratio of the starch half ester of an alkenyl succinic anhydride:oil of 1:6.

In another embodiment, a test oil-in-water emulsion is prepared using the starch emulsifier product as sole emulsifier, wherein the test oil-in-water emulsion has a 24% by weight oil load.

In another embodiment, an emulsion comprising an oil; a water; and a starch is described, wherein the starch is a half ester of an alkenyl succinic anhydride; wherein the starch is prepared by a dispersed phase process; wherein the starch is characterized by a water fluidity of no more than 75, and wherein the starch is characterizable by the following:

when the starch is used to prepare a test oil-in-water emulsion with the starch as a sole emulsifier at a w/w ratio of the starch:oil of 1:4 and an oil load of 20% by weight, the test oil-in-water emulsion is characterized by at least the following:

a. no more than about 5% of oil particles of the test oil-in-water emulsion greater than 1 micron after 24 hours at 57 C as assessed by polarization intensity differential plus elastic light scattering; and b. a Brookfield viscosity of the test oil-in-water emulsion of less than about 2000 cps after about one week of storage at 5 C, as assessed by Brookfield Programmable DV-1 Viscometer.

In another embodiment, an emulsion is disclosed comprising a starch; oil; and water; wherein the starch is a half ester of a dodecenyl succinic anhydride.

In another embodiment, an emulsion is disclosed comprising a starch; oil; and water; wherein the starch is a half ester of an octenyl succinic anhydride.

In another embodiment, an emulsion is disclosed comprising a starch; oil; and water; wherein the water fluidity of the starch is no greater than 65.

In another embodiment, an emulsion is disclosed comprising a starch; oil; and water; wherein the water fluidity of the starch is not greater than 40.

In another embodiment, an emulsion is disclosed comprising a starch; oil; and water; wherein the starch is a half ester of an octenyl succinic anhydride and the water fluidity of the starch is no greater than 40.

In another embodiment, an emulsion is disclosed, wherein the starch and the oil are present in the emulsion in a ratio of 1:4 and wherein the oil is present in an amount of 12% (w/w) based on the emulsion.

In another embodiment, an emulsion is disclosed, wherein the starch and the oil are present in the emulsion in a ratio of 1:4 and wherein the oil is present in an amount of 20% (w/w) based on the emulsion.

In another embodiment, an emulsion is disclosed, wherein the starch and the oil are present in the emulsion in a ratio of 1:4 and wherein the oil is present in an amount of 24% (w/w) based on the emulsion.

In another embodiment, an emulsion is disclosed, wherein the starch and the oil are present in the emulsion in a ratio of 1:6 and wherein the oil is present in an amount of 12% (w/w) based on the emulsion.

In another embodiment, an emulsion is disclosed, wherein the starch and the oil are present in the emulsion in a ratio of 1:6 and wherein the oil is present in an amount of 20% (w/w) based on the emulsion.

In another embodiment, an emulsion is disclosed, wherein the starch and the oil are present in the emulsion in a ratio of 1:6 and wherein the oil is present in an amount of 24% (w/w) based on the emulsion.

In another embodiment, an emulsion is disclosed comprising a starch; oil; and water; wherein the ratio of the starch to the oil is 1:6 and wherein the oil is present in an amount of 24% (w/w) based on the emulsion.

For the purposes of describing and claiming the present invention, the following terms are defined:

The term "half ester of an alkenyl succinic anhydride" means: a derivative prepared by chemical modification of a starch with an alkenyl succinic anhydride derivative. In one example, a half ester of an alkenyl succinic anhydride may be prepared by reacting an alcohol group present on a starch with a cyclic anhydride, thus opening the cyclic structure of the cyclic anhydride and forming a half-acid, half-ester, for example in the following diagram, where StOH=starch:

The term "alkenyl succinic anhydride" means: an organic compound with the molecular formula $RC_4H_3O_3$ wherein R is an alkenyl group. It is the acid anhydride of a substituted succinic acid.

The term "OSA" means octenyl succinic anhydride.

The term "Funnel Viscosity" means a viscosity test whereby the flow rate of a specific volume of a starch dispersion is measured using a precisely defined glass funnel according to the following procedure. Funnel Viscosity may be determined, in one embodiment, by adjusting the starch dispersion to be tested to 8.5% solids (w/w), measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow out of the funnel into the graduated cylinder to remove any trapped air and the balance is poured back into the funnel. The finger is then removed to allow the contents to flow out of the funnel and a timer is used to measure the time required for the 100 ml sample to flow through the apex (junction of the stem and funnel body) of the funnel. This time is recorded and is identified as the funnel viscosity, measured in seconds. The glass portion of the funnel is a standard 58°, thick-wall, resistance glass funnel whose top diameter is about 9 to about 10 cm with the inside diameter of the stem being about 0.381 cm. The glass stem of the funnel is cut to an approximate length of 2.86 cm from the apex, carefully fire-polished, and refitted with a long stainless steel tip which is about 5.08 cm long with an outside diameter of about 0.9525 cm. The interior diameter of the steel tip is about 0.5952 cm at the upper end where it is attached to the glass stem and about 0.4445 cm at the outflow end with the restriction in the width occurring at about 2.54 cm from the ends. The steel tip is attached to the glass funnel by means of a Teflon tube. The funnel is calibrated so as to allow 100 ml of water to go through in six seconds using the above procedure.

The term "water fluidity" means a test of viscosity measured on a scale of 0-90. Water fluidity is measured using a Bohlin Visco 88 Rotational Viscometer with water jacket (commercially available from Malvern Instruments, Inc., Southborough, Mass.), standardized at 30° C. with a standard oil having a viscosity of 100.0 cps. The water fluidity is obtained by determining the viscosity at a 8.06% solids level and converting that viscosity to a water fluidity (WF) value using the equation below. The procedure involves adding the required amount of starch (e.g., 10.0 g. dry basis) to a stainless steel cup and adding 14 g. distilled water to make a paste. Then 100.00 grams of a 20% $CaCl_2$ solution is added to the cup and the mixture is heated in a 100° C. water bath for 30 min. with rapid stirring for the first 2 minutes. The starch dispersion is then brought to the final weight (e.g. 124 g.) with 90° C. or hotter distilled water. The sample is immediately transferred to the viscometer cup, which is then placed into the Bohlin Visco 88 unit and analyzed for its viscosity at 90° C. (after the unit is calibrated). The viscosity (in mPa-s) recorded by the Bohlin Visco 88 unit is converted to a water fluidity number as defined by the following equation: $(WF=116.0-[18.746\times Ln(viscosity)])$, wherein Ln=natural logarithm.

For the purposes of the present invention, the relationship between funnel viscosity and water fluidity as each is measured according to the conditions described above is exemplified in the FIGURE.

The term "waxy" or "low amylose" means a starch or starch-containing product (herein starch or starch-containing product shall be referred to as starch) containing less than 10% amylose by weight, in one embodiment less than 5%, in another less than 2% and in yet another embodiment less than 1% amylose by weight of the starch.

The term "high amylose" means a starch containing at least 50% amylose by weight, in one embodiment at least 70%, in another at least 80% and in yet another embodiment at least 90% amylose by weight of the starch.

The term "starch containing product" means any product containing starch, including without limitation, flour and grits.

The term "oil load" is intended to mean the amount of oil in the emulsion based upon the entire emulsion and is measured on a weight percentage basis.

The term "Polarization Intensity Differential Plus Electric Light Scattering" means the use of the polarization effects of scattered light so as to estimate the particle size of very small objects. Vertically polarized scattered light has different scattering patterns and fine structures from that of horizontally polarized light for small particles. The main characteristic of the horizontal scattering intensity ($I_h$) for small particles is that there is a minimum around 90 degrees. This minimum shifts to larger angles for larger particles. Thus, although both vertical scattering intensity ($I_v$) and horizontal scattering intensity ($I_h$) have only small contrast in the case of small particles, the difference between them can reveal a more distinguished fine structure, thereby making the sizing of small particles possible. Combining polarization effects with wavelength dependence at large angles, the process may be extended to the lower sizing limit to as low as 40 nm without extrapolation. This combined approach is known as the Polarization Intensity Differential Scattering (PIDS) technique (Beckman Coulter). When the light beam is polarized in either the v direction or the h direction, the scattering intensity $I_v$ and $I_h$ for a given angle will be different. The difference between $I_v$ and $I_h$ ($I_v-I_h$) is termed the PIDS signal. For small particles the PIDS signal is roughly a quadratic curve centered at 90 degrees. For larger particles the pattern shifts to smaller angles and secondary peaks appear due to the scattering factor. Since the PIDS signal is dependent on particle size relative to light wavelength, valuable information about a particle size distribution can be obtained by measuring the PIDS signal at several wavelengths.

The term "Brookfield viscosity" means viscosity determined through measurements performed by the Brookfield Programmable DV-I Viscometer at given measurement conditions (spindle S63 @ 60 rpm with a reading taken 15 sec after the start of rotation) at room temperature (i.e. 22° C.). The principal of operation of the DV-I is to drive or rotate a spindle (which is immersed in the test fluid) through a calibrated spring. The viscous drag of the fluid against the spindle is measured by the spring deflection. Spring deflection is measured with a rotary transducer which translates the drag into viscosity of the test fluid through an internal calibration. The measurement range (in centipoises or milliPascal seconds) is determined by the rotational speed of the spindle, the size and shape of the spindle, the container (in one embodiment, an 8 ounce tall glass bottle having dimensions of 2.25" width×5" height) that the spindle is rotating in, and the full scale torque of the calibrated spring.

The term "test oil-in-water emulsion" means an emulsion prepared by the process by which a pre-emulsion is first made by slowly adding the oil blend to a starch dispersion (starch in aqueous phase) stirring with an LCI high shear mixer (Model HSM-100 LCI from Charles Ross & Son Company) at 5000 rpm for 2 minutes. The above pre-emulsion is subsequently homogenized by two passes through an APV pressure homogenizer (Model 15 MR Laboratory Homogenizer from APV Gaulin); with the second stage set at 500 psi and the first stage set at 3000 psi for 12% oil load, and with the second stage set at 500 psi and the first stage at 4500 psi for 20% oil load or 24% oil load.

The term "dispersed phase process" means: an at least 2 step process wherein a starch is sufficiently solubilized; then, in the next or any subsequent process step, the sufficiently solubilized starch is derivatized.

The term "sufficiently solubilized starch" means starch that is substantially gelatinized so that the starch does not have a Maltese cross when viewed under polarized light and has lost all of its granular or crystalline structure when viewed microscopically at 100× magnification. In a more specific embodiment, "Sufficiently Solubilized Starch" means starch having an average particle size of less than one micron, as assessed by Polarization Intensity Differential Plus Elastic Light Scattering (Beckman Coulter LS 13 320 Aqueous Model).

DETAILED DESCRIPTION OF THE INVENTION

Figure 1:
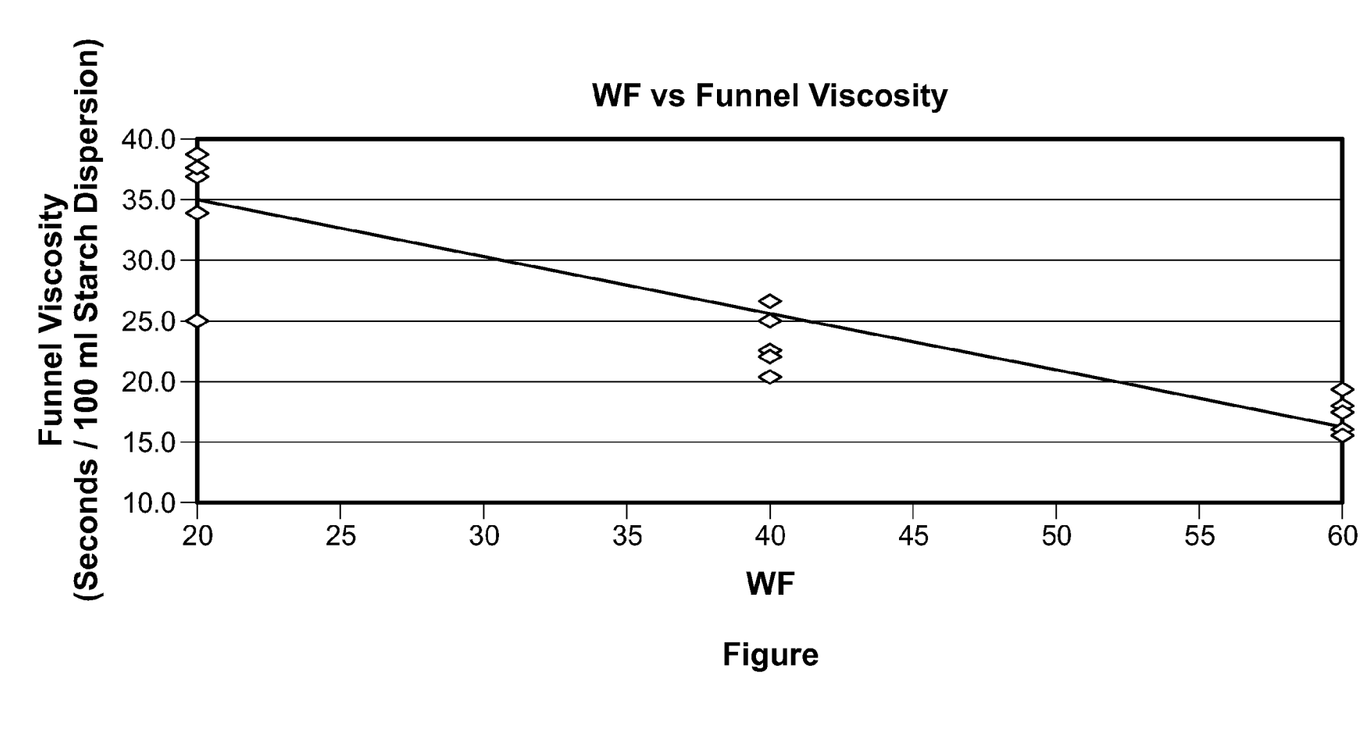
The FIGURE depicts an embodiment of a graphical description of the relationship between funnel viscosity and water fluidity, as each is measured according to the conditions described herein.

Detailed embodiments of the present invention are described herein; however, it is to be understood that the disclosed embodiments are merely illustrative of the invention that may be embodied in various forms. In addition, each of the examples given in connection with the various embodiments of the invention are intended to be illustrative, and not restrictive. Further, the FIGURE is not necessarily to scale, and some features may be exaggerated to show details of particular components. In addition, any measurements, specifications and the like shown in the FIGURE are intended to be illustrative, and not restrictive. Therefore, specific structural and/or functional details disclosed herein are not to be interpreted as limiting, but merely as a representative basis for teaching one skilled in the art to variously employ the present invention.

In one embodiment of the present invention, starch is first slurried in an aqueous phase, yielding a slurry of approximately 40% as-is starch solids (approximately 35% dry solids) and then is heated to 54° C. (129.2° F.). The starch is then acid converted. In one embodiment of the present invention, 0.7% concentrated HCl is added to the slurried starch, the slurry is mixed for 16 hours and is then neutralized to pH 5.5 with 3% NaOH. The starch is then filtered and washed and dried, and then re-suspended to form a slurry of approximately 40% as-is starch solids. In one embodiment, the slurry is then continuously jet cooked at approximately 310° F. 154° C. (310° F.), resulting in a sufficiently solubilized starch with a dry solids content of 30%. Thereafter, the sufficiently solubilized starch is sufficiently derivatized. In one embodiment, the sufficiently solubilized waxy maize starch is placed in a constant temperature bath and maintained at 40° C. (310° F.), with constant stirring. The pH is, in one embodiment, adjusted to 7.5 with 3% NaOH. Then, 3% OSA, by weight based on the weight of "as-is" starch, was slowly added to the solubilized starch while the pH was maintained at 7.5. After the reaction is completed, the pH is neutralized to 5.5 with dilute HCl. Following sufficient derivatization, the starch may then be optionally enzyme converted and/or spray-dried. At the conclusion of the preparation steps described above, the emulsifier product of the present invention has a water fluidity of no more than 75, and is characterized with the following test oil-in-water emulsion: when the starch half ester of an alkenyl succinic anhydride is used to prepare a test oil-in-water emulsion with the starch as a sole emulsifier at a w/w ratio of the starch:oil of 1:4 and oil load of 12%, the test oil-in-water emulsion is characterized by at least the following: 1. no more than about 5% of oil particles of the test emulsion greater than 1 micron after 24 hours at 57° C. (134.6° F.) as assessed by polarization intensity differential plus elastic light scattering; and 2. a Brookfield viscosity of the test emulsion of less than about 2000 cps after about one week of storage at 5° C. (41° F.), as assessed by Brookfield Programmable DV-1 Viscometer.

Suitable starch sources for the invention may be derived from any native source. A native source as used herein, is one as it is found in nature. Also suitable are starches derived from a plant obtained by standard breeding techniques including crossbreeding, translocation, inversion, transformation or any other method of gene or chromosome engineering to include variations thereof which are typically referred to as genetically modified organisms (GMO). In addition, starch derived from a plant grown from artificial mutations and variations of the above generic composition, which may be produced by known standard methods of mutation breeding, are also suitable herein.

Typical sources for the starches are cereals (grains), seeds, tubers, roots, legumes and fruits. The native source can be corn (maize), pea, potato, sweet potato, banana, barley, wheat, rice, oat, sago, amaranth, tapioca (cassava), arrowroot, canna, and sorghum as well as waxy or high amylose varieties thereof. The invention embodied within relates to all starches regardless of amylose content and is intended to include all starch sources, including those which are natural, genetically altered or obtained from hybrid breeding. In one embodiment, the starch is a waxy starch and in another embodiment is a waxy corn starch.

In one embodiment of the present invention, starch is acid converted.

The starch is solubilized. The starch may be solubilized, for example, by chemical, enzymatic or physical processing.

In one embodiment of the present invention, the solubilization may result in a converted starch. The conversion may be to any degree so long as the emulsifier product of the present invention does not have a water fluidity greater than 75.

Suitable methods for sufficiently solubilizing the starch include, but are not limited to, "jet-cooking," for example, utilizing a Hydroheater (Hydro-Thermal Corporation, Milwaukee, Wis.) cooking chamber at approximately 154° C. (310° F.); placing the granular starch in boiling water; treating the granular starch with a caustic agent; treating the granular starch with a salt including but not limited to urea; and/or physical destruction of the starch granules.

The solubilized starch is chemically derivatized.

In yet another embodiment, the reagent has an alkyl or an alkenyl group which contains at least five carbon atoms or an aralkyl or aralkenyl group which contains at least six carbon atoms, and in one embodiment may contain up to twenty-four carbon atoms.

Suitable reagents for sufficiently derivatizing a sufficiently solubilized starch so as to yield a starch half ester of an alkenyl succinic anhydride meeting the criteria outlined above include, but are not limited to, octenyl succinic anhydride, dodecenyl succinic anhydride and various cyclic dicarboxylic acid anhydrides. In one embodiment, the reagent is octenyl succinic anhydride or dodecenyl succinic anhydride and in another embodiment is octenyl succinic anhydride.

Reagents include without limitation imidazolides, N,N'-disubstituted imidazolium salts of carboxylic or sulfonic acids, quaternary or tertiary amines, acetic anhydride, alkylene oxides, and succinic anhydrides.

One or more process steps may be performed between (1) sufficiently solubilizing the starch and (2) sufficiently derivatizing the sufficiently solubilized starch described herein, including but not limited to acid conversion, oxidation, etc., so long as the process steps intervening between the sufficiently solubilizing and sufficiently derivatizing steps outlined above do not render the derivatizing step insufficient in yielding the emulsifier product of the present invention (for example, by further degrading the sufficiently solubilized starch so as to yield an abundance of oligosaccharide degradation byproducts).

In another embodiment of the present invention, the solubilized material is treated with phosphoric acid before and/or after the derivatization step.

The starch may be converted to reduce the viscosity of the emulsifier product of the present invention.

In one embodiment, conversion is by acid degradation.

In one embodiment, conversion is by heat.

In one embodiment, conversion is by shear.

The conversion may be conducted either before or after the derivatization. In one embodiment, the conversion is before derivatization.

The conversion may be to any degree so long as the emulsifier product of the present invention does not have a water fluidity greater than 75.

In a further embodiment, the starch is not intentionally converted.

In one embodiment of the present invention, the starch may be treated with any enzyme at any time subsequent to derivatization of the solubilized starch or with an enzyme (such as alpha amylase) that randomly cleaves $\alpha(1\text{-}4)$ glycosidic linkages prior to derivatization of the starch. Enzymes useful for treatment after derivatization would include but are not limited to alpha-amylase, beta-amylase, glucoamylase, maltogenase, pullulanase, exo-alpha-1,4-glucosidase, exo-1,4-alpha-D-glucan maltotetrahydrolase, and exo-1,4-alpha-D glucan maltohexahydrolase.

The starch may be further treated by enzyme after the starch has been solubilized and derivatized. When the desired conversion is reached, the enzyme may be deactivated by heat or pH. Thereafter the pH may be readjusted. The type and concentration of the enzyme, the conversion conditions, and the length of conversion all will contribute to the composition of the resultant product. In the alternative, a combination of enzymes may be used.

In another embodiment of the present invention, the starch may be enzyme converted at any time so long as the emulsifier product of the present invention is still capable of sufficient derivatization so as to effectively function as an emulsifier with respect to the above-identified test emulsion.

The pH of the derivatized starch may be adjusted to the desired pH according to its intended end use. In one embodiment, the pH is adjusted to from 5.0 to 7.5, and in another embodiment from 6.0 to 7.0, using techniques known in the art.

The starch may be purified to remove impurities, by-products, off-flavors and colors by methods known in the art including without limitation by washing, dialysis, filtration, ion exchange processes, steam stripping, bleaching such as by chlorites, and/or centrifugation. Such purification may be done at any time in the process as long as the purification does not adversely affect the requirements of the starch emulsifier.

The derivatized starch may be used as is in its liquid form or it may be dried using methods known in the art including without limitation drum drying, spray drying, freeze drying, and/or air drying.

In another embodiment, any of the above process steps may be used individually and/or in combination with any optional steps such as conversion by acid, heat, shear, oxidation, bleaching, enzyme treatment, and/or any combination thereof. However, any method or combination of methods must result in an emulsifier product of the present invention with a water fluidity of no greater than 75 and characterized in the following test oil-in-water emulsion:

when the starch half ester of an alkenyl succinic anhydride is used to prepare a test oil-in-water emulsion with the starch as a sole emulsifier at a w/w ratio of the starch:oil of 1:4 and an oil load of 20%, the test oil-in-water emulsion is characterized by at least the following:

1. no more than about 5% of oil particles of the test emulsion greater than 1 micron after 24 hours at 57° C. (134.6° F.) as assessed by polarization intensity differential plus elastic light scattering; and 2. a Brookfield viscosity of the test emulsion of less than about 2000 cps after about one week of storage at 5° C. (41° F.), as assessed by Brookfield Programmable DV-1 Viscometer.

The water fluidity of the emulsifier product is not greater than 75. In one embodiment the emulsifier product of the present invention has a water fluidity of not greater than 65, and in yet another embodiment the emulsifier product of the present invention has a water fluidity of not greater than 40. In one embodiment the emulsifier product of the present invention has a water fluidity of between 11-20 WF, in another embodiment the emulsifier product of the present invention has a water fluidity of between 11-40, in yet another embodiment the emulsifier product of the present invention has a water fluidity of between 11-65, in a further embodiment the emulsifier product of the present invention has a water fluidity of between 20-40, in a still further embodiment the emulsifier product of the present invention has a water fluidity of between 20-65, and in yet one further embodiment the emulsifier product of the present invention has a water fluidity of between 40-65.

The emulsifier product may be used to prepare an oil-in-water emulsion by mixing it with an oil. The oil may include an oil-based active agent including without limitation flavors, colors, fragrances, pharmaceuticals and/or vitamins. Oil is also intended to include triglycerides such as medium chain triglycerides.

The oil may be present in the emulsion in any desirable amount possible and the oil load will depend upon many parameters, but specifically upon the amount of emulsifier starch product used. In one embodiment the oil load is 12%, in another embodiment 20%, and in yet another embodiment 24% by weight of the emulsion.

The starch:oil ratio of the emulsion may also be any desirable ratio and will also depend upon many parameters. In one embodiment, the starch:oil ratio is 1:1, in another embodiment 1:3, in yet another embodiment 1:4 and in still yet another embodiment 1:6, all on a weight:weight basis.

Other optional ingredients may be added to the emulsion. In one embodiment, an antioxidizing agent is added to the dispersed (oil) phase.

In another embodiment, a pre-emulsion is prepared prior to the emulsion.

The emulsion may also be made into an encapsulated form by techniques known in the art including but not limited to spray drying, extruding, and spray chilling.

The encapsulated product may be effectively stored as a powder and spontaneously releases the encapsulant upon exposure to significant moisture, such as when added to water.

The emulsion or encapsulated product may be used at any level desired in a variety of products. The products include without limitation food and beverage products, pharmaceuticals, nutraceuticals, infant products, paper products, animal care products, household products, agricultural products, and personal care products.

Food and beverage products include, but are not limited to juice beverages, sodas; instant coffees and teas; sauce and gravies; soups; cereals; dressings; bakery products; instant and cook-up mixes; nondairy creamers; salad dressings; and sweetened condensed creamers.

Personal care products include without limitation antiperspirants, deodorants, soaps, fragrances, and cosmetics; hair care products, such as hair sprays, mousses, shampoos, cream rinses, bath products, and gels.

Paper products include without limitation diapers, sanitary napkins, paper towels, tissues, and toilet tissues.

Animal care products include without limitation animal foods and kitty litter.

Household products include without limitation cleaners, detergents, fabric softeners, and air fresheners.

Unless indicated otherwise, all percentages and/or ratios expressed in the below examples and/or preparations are weight/weight. Water fluidity and funnel viscosity measurements were, absent indication otherwise, obtained using the protocols outlined above. Unless indicated otherwise, all percent OSAs are by weight, based on the weight of starch as is.

Preparation of Orange Oil Emulsions

Orange Oil emulsions were prepared as follows:

| Formula 1: Flavor Oil Composition | |
|---|---|
| Ingredients: | % |
| Orange Oil (1×) | 48 |
| Orange Oil (5×) | 12 |
| Ester Gum | 40 |

1× (one fold) and 5× (five fold) orange oil were combined. An ester gum was added to the 1×/5× orange oil blend and dissolved using mechanical agitation at room temperature. It was confirmed that all ester gum was dissolved thoroughly, at an approximate timepoint of 3 hours.

| Formula 2: Standard Orange Oil Emulsion Utilizing Flavor Oil Composition | |
|---|---|
| Ingredients | |
| Flavor Oil (Formula 1) | 12%-24% |
| Stabilizer | 2%-12% |
| Sodium Benzoate | 0.15% |
| Citric Acid | 0.30% |
| Water | Up to 100% |

The required amounts of sodium benzoate were dissolved in water. Citric acid was dissolved in the above solution. Starch was dispersed with moderate agitation. A pre-emulsion and then an emulsion was made using the procedure set forth for a test oil-in-water emulsion.

Procedure for Measurement of Emulsion Particle Size

Emulsion particle sizes were measured using the LS 13 230, manufactured by Beckman Coulter and incorporating Polarization Intensity Differential Screening technology together with a sophisticated software package to provide a dynamic range of particle size measurement capabilities between 0.04 µm to 2000 µm.

From the pull down manual of the software, we entered sample ID and selected the appropriate optical module to be used for the system to be measured. A sequence of steps automatically followed: Measuring offsets; Alignment; Background measurement; Measure loading. The instrument sounded a bell and displayed Measuring Loading when ready to accept a sample.

A diluted sample was introduced by drops into the sample reservoir and changes in the Measure Loading were observed. This function measured the amount of light scattered out of the beam by the particles so as to determine an appropriate concentration of sample. When sizing particles without using PIDS an obscuration level of 8% to 12% is appropriate. When PIDS is used, a PIDS obscuration of 40% to 60% is recommended. A real part of index of refraction of 1.5 was used.

Analysis then followed. The pull-down menu allowed the user to print the results and related graphs either to the inline printer or to a PDF file.

Procedure for Measurement of Emulsion Viscosity

Viscosity measurements were performed with the Brookfield Programmable DV-I Viscometer at a given measurement conditions (spindle S63 @ 60 rpm with a reading taken 15 seconds after the start of rotation). The principal of operation of the DV-I is to drive or rotate a spindle (which is immersed in the test fluid) through a calibrated spring. The viscous drag of the fluid against the spindle is measured by the spring deflection. Spring deflection is measured with a rotary transducer which translates the drag into viscosity of the test fluid through an internal calibration. The measurement range (in centipoises or milliPascal seconds) is determined by the rotational speed of the spindle, the size and shape of the spindle, the container the spindle is rotating in, and the full scale torque of the calibrated spring. Viscosity measurements were made on a 22° C. (71.6° F.) sample contained in an 8 ounce tall glass fluid container having dimensions of 2.25" width× 5" height. The Viscometer was leveled and warmed up for ~10 minutes. The selected spindle was rotated through the sample of interest for a predetermined time period (15 seconds). The viscosity of the test fluid was displayed in centipoises.

Example 1

Comparison of Test Emulsions

The effectiveness of the starch emulsifier products of the present invention in emulsifying a high oil load/emulsifier ratio and in maintaining a stable emulsion viscosity were examined as set forth in TABLE 1. All samples below in TABLE 1 were prepared using emulsifiers utilized as sole emulsifiers and prepared using one of two methods: (1) OSA-derivatized dispersed phase (DP) emulsifiers, in which (a) granular starch was (b) slurried in aqueous solution; (c) solubilized via jet-cooking; (d) in some step subsequent to solubilization, derivatized with OSA; and (e) spray-dried; or (2) OSA-derivatized granular emulsifiers, in which (a) granular starch was (b) slurried in aqueous solution; (c) derivatized with OSA; (d) in some step subsequent to derivatization with OSA, solubilized via jet cooking; and (e) spray-dried. N3700=NATIONAL® 3700 starch PG 2000=PURITY® GUM 2000 starch; PG 1773=PURITY® GUM 1773 starch (all three starches are commercially available from National Starch LLC, Bridgewater, N.J.). (ETENIA™ is a trademark of and is commercially available from AVEBE, Veendm, the Netherlands).

TABLE 1

Comparison Of Test Emulsions Prepared With OSA-Derivatized Granular Starches And OSA-Derivatized Solubilized Starches Prepared According To Example 1

| Starch | WF | % Oil Load | Ratio (starch:oil) | % > 1 micron at 57° C., 24 hrs. | % > 1 micron at 43.3° C., 8 days | Brookfield viscosity/5° C. (sp 3/60 rpm) (1 week in refrigerator) |
|---|---|---|---|---|---|---|
| DP | 20 | 24 | 1:6 | <5% | <5% | <2000 cpc |
| DP | 20 | 12 | 1:6 | <5% | <5% | <2000 cpc |
| DP | 40 | 24 | 1:5 | <5% | <5% | <2000 cpc |
| DP | 60 | 24 | 1:4 | <5% | <5% | <2000 cpc |
| DP | 60 | 24 | 1:5 | <5% | <5% | <2000 cpc |
| DP | 60 | 24 | 1:6 | <5% | <5% | <2000 cpc |
| DP | 80 | 12 | 1:6 | <5% | <5% | <2000 cpc |
| DP | 80 | 12 | 1:1 | Emulsion broke 100% | Emulsion broke 100% | not tested |
| DP | 80 | 12 | 1:2 | Emulsion broke 100% | Emulsion broke 100% | not tested |
| DP | 85 | 12 | 1:1 | Emulsion broke 100% | Emulsion broke 100% | not tested |
| Granular | 20 | 24 | 1:6 | 16.8 | not measured | <2000 cpc |
| Granular | 20 | 20 | 1:5 | not measured | 9.32 | <2000 cpc |
| Granular | 20 | 12 | 1:6 | 8.91 | not measured | <2000 cpc |
| Granular | 40 | 24 | 1:5 | 15.9 | not measured | <2000 cpc |
| Granular | 40 | 20 | 1:2.5 | not measured | 55.3 | <2000 cpc |
| Granular | 40 | 12 | 1:6 | 15.1 | not measured | <2000 cpc |
| Granular | 60 | 24 | 1:4 | 10.6 | not measured | <2000 cpc |
| Granular | 60 | 20 | 1:2.4 | not measured | 21.5 | <2000 cpc |
| Granular | 60 | 12 | 1:6 | 10.7 | not measured | <2000 cpc |

TABLE 1-continued

Comparison Of Test Emulsions Prepared With OSA-Derivatized
Granular Starches And OSA-Derivatized Solubilized Starches Prepared According
To Example 1

| Starch | WF | % Oil Load | Ratio (starch:oil) | % > 1 micron at 57° C., 24 hrs. | % > 1 micron at 43.3° C., 8 days | Brookfield viscosity/5° C. (sp 3/60 rpm) (1 week in refrigerator) |
|---|---|---|---|---|---|---|
| Granular | 80 | 12 | 1:1 | not measured | 11.7 | <2000 cpc |
| Granular | 80 | 12 | 1:2 | Emulsion broke 100% | Emulsion broke 100% | not tested |
| Granular | 85 | 12 | 1:1 | Emulsion broke 100% | Emulsion broke 100% | not tested |
| N3700 | 65 | 24 | 1:4 | 10.5 | 16.3 | gelled/>2000 cpc |
| N3700 | — | 24 | 1:5 | 21.5 | 20.2 | gelled/>2000 cpc |
| PG2000 | 80 | 24 | 1:2 | 21 | 22.9 | <2000 cpc |
| PG1773 | 80 | 24 | 1:2 | 6.1 | 14 | gelled/>2000 cpc |
| EmCap 12633 | 80 | 24 | 1:6 | 19.2 | 23.6 | <2000 cpc |
| EmCap 12633 | 80 | 24 | 1:4 | 8.25 | 8.41 | <2000 cpc |
| EmCap 12633 | 80 | 24 | 1:3 | 6.04 | 7.32 | gelled/>2000 cpc |
| ETENIA™ derivatized with 3% OSA | 73 | 24 | 1:4 | 0 | 0 | gelled |
| ETENIA™ derivatized with 4% OSA | 73 | 24 | 1:4 | 0 | 0 | gelled/>2000 cpc |

The above TABLE 1 demonstrates that the present invention had unexpected results, as the emulsifier of the present invention demonstrated substantial improvements in emulsifying characteristics as compared to (a) OSA-derivatized granular emulsifiers with varying water fluidities; (b) OSA-derivatized dispersed phase emulsifiers with water fluidities above 75; and (c) OSA-derivatized gelling starches (e.g., ETENIA™).

Example 2

High Oil Load Emulsion Performance

High oil load (24%) performance of emulsifiers of the invention prepared using various OSA-derivatized dispersed phase emulsifiers derived from various starch sources and subject to high oil load (24%) emulsion conditions were assessed. Samples were prepared by slurrying 8 kg (anhydrous basis) starch in 12 liters tap water. This slurry was then jet cooked, using a Hydroheater (Hydro-Thermal Corporation, Milwaukee, Wis.) cooking chamber at approximately 154° C. (310° F.), resulting in a 30% solids jet cooked starch dispersion (after slight dilution—one waxy corn starch cook was run at 24.5% solids).

The cook was divided into three 8 liter stainless steel beakers, and placed in a hot water bath at 90° C. (194° F.). To each was added 0.075% concentrated HCl (on as-is starch weight). The funnel viscosity was tracked over time until the desired range was reached.

The OSA derivatization reaction was carried out on these dispersions in stainless steel beakers placed in an immersion circulator bath to maintain the temperature at 55° C. (waxy corn reactions were run at 59° C. and 76° C. (138.2° F. and 168.8° F.). The pH of each was adjusted to 7.5 with 3% NaOH. Then 2.5% OSA reagent (1.75% for sample 2)(2.5% OSA reagent is equivalent to 2.84% OSA (dry basis) on dry starch) on as-is starch weight was added drop-wise to each dispersion while the pH was maintained at 7.5, using 3% NaOH. When no 3% NaOH was needed to keep the pH at 7.5 for a 30 minute period (indicating that the OSA reaction with starch was completed), the dispersion was then adjusted to pH 5.8 with dilute HCl. The product was then spray-dried.

TABLE 2, below, depicts characteristics of various examples of emulsions prepared utilizing emulsifier products of the present invention, These examples include emulsifier products of the present invention derived from a variety of starch sources, including waxy corn starch. Starch-to-oil ratio of the various test emulsions described in TABLE 2 may be derived by dividing the "% starch solids" indicated for each emulsion by the oil load of 24%. SS=starch solids; P.S.=particle size (in all instances, measured in microns (mμ)).

WAXIPRO® is a registered trademark denoting a product sold by National Starch, LLC, Bridgewater, N.J. Sample 2 (Waxy Corn) was prepared by utilizing an acid-converted waxy corn starch that was re-suspended, jet cooked, reacted with 2.5% OSA in the dispersed phase, neutralized to pH 6.03 and spray dried.

TABLE 2

Emulsions Prepared Utilizing Dispersed Phase Process

| Starch Base | Preparation Conditions | % OSA Treatment | Funnel Viscosity (spray-dried) | % Starch Solids | P.S. (Fresh) | | | P.S. (1 days @ 57° C.) | | | P.S. (8 days @ 110 F.) | | |
|---|---|---|---|---|---|---|---|---|---|---|---|---|---|
| | | | | | Median (μm) | Mean (μm) | >1 micron | Median (μm) | Mean (μm) | >1 micron | Median (μm) | Mean (μm) | >1 micron |
| 1. Waxy Corn | 30% SS, pH 7, 59° C. | 2.84 | 19.27 | 6 | 0.22 | 0.19 | 0 | 0.231 | 0.199 | 0 | 0.266 | 0.244 | 0 |
| 2. Waxy Corn* | 24.5% SS, pH 7, 76° C. | 2.00 | 32.09 | 4 | 0.255 | 0.235 | 0 | 0.268 | 0.247 | 0 | 0.275 | 0.256 | 0 |
| 3. Waxy Potato | 30% SS, pH 7, 55° C. | 2.84 | 13.49 | 6 | 0.214 | 0.198 | 0 | 0.302 | 0.289 | 0 | 0.348 | 0.327 | 0 |
| 4. Waxy Potato | 30% SS, pH 7, 55° C. | 2.84 | 28.24 | 5 | 0.244 | 0.224 | 0 | 0.283 | 0.268 | 0 | 0.312 | 0.294 | 0 |
| 5. Waxy Potato | 30% SS, pH 7, 55° C. | 2.84 | 31.55 | 4 | 0.307 | 0.294 | 0 | 0.32 | 0.301 | 0 | 0.287 | 0.268 | 0 |
| 6. WAXIPRO® | 30% SS, pH 7, 55° C. | 2.84 | 19.50 | 6 | 0.227 | 0.2 | 0 | 0.241 | 0.215 | 0 | 0.234 | 0.202 | 0 |
| 7. WAXIPRO® | 30% SS, pH 7, 55° C. | 2.84 | 28.26 | 5 | 0.285 | 0.271 | 0 | 0.272 | 0.254 | 0 | 0.283 | 0.262 | 0 |

Example 3

Comparison of Brookfield Viscosity, Oil Particle Size and Oil Load of Various Single-Emulsifier Emulsion Preparations Example 3A Dispersed, OSA-Derivatized, then Enzyme Converted Starch Emulsifier This example illustrates the preparation of an enzyme-converted starch of the invention for use in beverage flavor emulsification. An OSA-derivatized dispersed phase emulsifier was prepared by first slurrying waxy maize starch at 40% as-is solids in tap water and adding 0.25% phosphoric acid on starch weight to the slurry. This slurry was then jet cooked at approximately 154° C. (310° F.), resulting in a solubilized starch dispersion with dry solids of 30%. Thereafter, the solubilized starch dispersion was placed in a constant temperature bath and maintained at 40° C. (104° F.) with constant stirring. Then 2.5% OSA reagent on as-is starch weight was added drop-wise over a 2 hour period to the solubilized starch so as to derivatize the solubilized starch. During the OSA derivatization step, the pH was maintained at 7.5, using 3% NaOH. When no additional 3% NaOH was needed to keep the pH at 7.5 for a 30 minute period (indicating that the OSA derivatization reaction with starch was completed), the dispersion was then adjusted to pH 5.5 with dilute HCl.

The above dispersion was then adjusted to pH 6.5, the temperature increased to 55° C. and 0.3% OPTIMALT® BBA β-amylase (available from Genencor International, Inc.) was added on starch weight.

The degree of starch degradation by β-amylase was correlated to the loss in viscosity. In this example, the desired enzyme reaction end point was reached with a funnel viscosity of 12.7 seconds (measured at 19% solids instead of 8.5% solids, as this product was low in viscosity). When the targeted viscosity was reached, the enzyme was deactivated by reducing the pH to 2.7 and holding for 30 min. to denature the enzyme. The sample was then adjusted to pH 4 and spray-dried at an inlet temperature of 200°-210° C. (392°-410° F.) and an outlet temperature of 85°-90° C. (185°-194° F.) using a standard #22 11/4 J nozzle obtained from Spraying Systems Company.

Example 3B

Dispersed, Enzyme Converted, then OSA-Derivatized Starch Emulsifier

This material was prepared identically as per Example 3A, with the exception that 0.3% OPTIMALT® BBA β-amylase treatment occurred prior to OSA derivatization of the starch.

Example 3C

Performance Comparisons of the Emulsifiers Made in Examples 3A and 3B

Orange oil emulsions using the starch emulsifier products made as per Examples 3A and 3B were prepared as follows:

250 g of each spray-dried starch was blended with 583.3 g of distilled water in a bench top mixer. While the mixer was agitating for 2 minutes at a speed dial setting of 30, single fold orange oil (166.7 g of single fold orange oil obtained from Givaudan) was added to the center of the vortex. After addition of the oil, the speed was increased to the highest setting and mixed for an additional 3 minutes.

While emulsifier products of the present invention made as per Example 3A produced an emulsion that had a mean particle size of 0.835 microns and its emulsion did not separate after 18 hours, emulsifiers made as per Example 3B produced an emulsion that had a mean particle size of 11.57 microns and its emulsion showed 15 mL of oil separation after only 2 hours.

While a number of embodiments of the present invention have been described, it is understood that these embodiments are illustrative only, and not restrictive, and that many modifications and/or alternative embodiments may become apparent to those of ordinary skill in the art. Therefore, it will be understood that the appended claims are intended to cover all such modifications and embodiments that come within the spirit and scope of the present invention.

What is claimed is:

1. An emulsifier product comprising:
A starch half ester of an alkenyl succinic anhydride,
wherein the starch half ester of the alkenyl succinic anhydride has a water fluidity of not more than 75 at a 8.06% solids level,
wherein the starch half ester of the alkenyl succinic anhydride is prepared by a dispersed phase process, and
wherein, when the starch half ester of an alkenyl succinic anhydride is used to prepare a test oil-in-water emulsion,
the test oil-in-water emulsion is characterized by at least the following:
   a) no more than about 5% of the oil particles of the emulsion greater than 1 μm after 24 hours at 57 C as assessed by polarization intensity differential plus elastic light scattering; and
   b) a Brookfield viscosity of the emulsion of less than about 2000 cps after about one week of storage at 5 C, as assessed by Brookfield Programmable DV-1 Viscometer; and
wherein the test oil-in-water emulsion is prepared with the starch half ester of an alkenyl succinic anhydride as a sole emulsifier;
at a w/w ratio of the starch half ester of an alkenyl succinic anhydride:oil of 1:4;
at a 20% by weight oil load; and
with the oil consisting of 48% 1× orange oil; 12% 5× orange oil; and 40% ester gum weight/weight.

2. The emulsifier product of claim 1, wherein the starch is a half ester of an octenyl succinic anhydride.

3. The emulsifier product of claim 1, wherein the water fluidity of the starch is not greater than 65.

4. The emulsifier product of claim 1, wherein the water fluidity of the starch is not greater than 40.

5. The emulsifier product of claim 1, wherein the water fluidity of the starch is not greater than 20.

6. The emulsifier product of claim 1, wherein the starch is a half ester of an octenyl succinic anhydride and the water fluidity of the starch is not greater than 40.

7. The emulsifier product of claim 1, wherein the average particle size of the emulsifier product may be characterized as less than one μm, as assessed by Polarization Intensity Differential Plus Elastic Light Scattering (Beckman Coulter LS 13 320 Aqueous Module).

8. The emulsifier product of claim 1, wherein, when the starch half ester of an alkenyl succinic anhydride is used to prepare the test oil-in-water emulsion having a w/w ratio of the starch half ester of an alkenyl succinic anhydride:oil of 1:6;
the test oil-in-water emulsion is characterized by at least the following:
properties characterized as said a) and said b); and
wherein the test oil-in-water emulsion is prepared with the starch half ester of an alkenyl succinic anhydride as a sole emulsifier;
at a w/w ratio of the starch half ester of an alkenyl succinic anhydride:oil of 1:6;
at a 20% by weight oil load;
and with the oil consisting of 48% 1× orange oil; 12% 5× orange oil; and 40% ester gum weight/weight.

9. The emulsifier product of claim 1, wherein, when the starch half ester of an alkenyl succinic anhydride is used to prepare the test oil-in-water-emulsion having a 24% by weight oil load;
the test oil-in-water emulsion is characterized by at least the following:
properties characterized as said a) and said b); and
wherein the test oil-in-water emulsion is prepared with the starch half ester of an alkenyl succinic anhydride as a sole emulsifier;
at a w/w ratio of the starch half ester of an alkenyl succinic anhydride:oil of 1:4;
at a 24% by weight oil load;
and with the oil consisting of 48% 1× orange oil; 12% 5× orange oil; and 40% ester gum weight/weight.

10. An emulsion comprising
an oil;
a water; and
the emulsifier product of claim 1.

11. The emulsion of claim 10, wherein the emulsifier product is a half ester of an octenyl succinic anhydride.

12. The emulsion of claim 10, wherein the water fluidity of the emulsifier product is not greater than 65.

13. The emulsion of claim 10, wherein the water fluidity of the emulsifier product is not greater than 40.

14. The emulsion of claim 10, wherein the emulsifier product is a half ester of an octenyl succinic anhydride and the water fluidity of the emulsifier product is not greater than 40.

15. The emulsion of claim 10, wherein the emulsifier product and the oil are present in the emulsion in a ratio of 1:4 and wherein the oil is present in an amount of 12% (w/w) based on the emulsion.

16. The emulsion of claim 10, wherein the starch and the oil are present in the emulsion in a ratio of 1:4 and wherein the oil is present in an amount of 20% (w/w) based on the emulsion.

17. The emulsion of claim 10, wherein the emulsifier product and the oil are present in the emulsion in a ratio of 1:4 and wherein the oil is present in an amount of 24% (w/w) based on the emulsion.

18. The emulsion of claim 10, wherein the emulsifier product and the oil are present in the emulsion in a ratio of 1:6 and wherein the oil is present in an amount of 12% (w/w) based on the emulsion.

19. The emulsion of claim 10, wherein the emulsifier product and the oil are present in the emulsion in a ratio of 1:6 and wherein the oil is present in an amount of 20% (w/w) based on the emulsion.

20. The emulsion of claim 10, wherein the emulsifier product and the oil are present in the emulsion in a ratio of 1:6 and wherein the oil is present in an amount of 24% (w/w) based on the emulsion.

* * * * *